United States Patent
Pacetti

(10) Patent No.: US 8,852,260 B2
(45) Date of Patent: Oct. 7, 2014

(54) DRUG-ELUTING STENT AND DELIVERY SYSTEM WITH TAPERED STENT IN SHOULDER REGION

(71) Applicant: Abbott Cardiovascular Systems Inc., Santa Clara, CA (US)

(72) Inventor: Stephen Dirk Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/017,548

(22) Filed: Sep. 4, 2013

(65) Prior Publication Data

US 2014/0172063 A1   Jun. 19, 2014

Related U.S. Application Data

(62) Division of application No. 13/727,327, filed on Dec. 26, 2012, now Pat. No. 8,551,152, which is a division of application No. 13/285,627, filed on Oct. 31, 2011, now Pat. No. 8,343,206, which is a division of application No. 11/646,781, filed on Dec. 28, 2006, now Pat. No. 8,057,526, which is a division of application No. 10/353,219, filed on Jan. 27, 2003, now Pat. No. 7,156,869.

(51) Int. Cl.
*A61F 2/06* (2013.01)
*A61L 31/16* (2006.01)
*A61F 2/915* (2013.01)
*A61F 2/82* (2013.01)
*A61F 2/91* (2013.01)
*A61F 2/958* (2013.01)

(52) U.S. Cl.
CPC ............... *A61L 31/16* (2013.01); *A61F 2/915* (2013.01); *A61F 2002/9583* (2013.01); *A61F 2002/91533* (2013.01); *A61F 2/82* (2013.01); *A61F 2002/91516* (2013.01); *A61F 2250/0067* (2013.01); *A61F 2/958* (2013.01); *A61F 2/91* (2013.01); *A61F 2002/91575* (2013.01)
USPC .......................................... 623/1.11; 606/108

(58) Field of Classification Search
CPC ............ A61F 2/958; A61F 2250/0048; A61B 5/6853
USPC .................. 623/1.11, 1.15; 606/108, 159, 198
See application file for complete search history.

(56) References Cited

U.S. PATENT DOCUMENTS 5,662,712 A * 9/1997 Pathak et al. .............. 623/23.64
5,713,853 A   2/1998 Clark et al.
(Continued)

*Primary Examiner* — Victor Nguyen
(74) *Attorney, Agent, or Firm* — Fulwider Patton LLP

(57) ABSTRACT

A drug-eluting stent delivery system for the treatment of edge restenosis in a blood vessel. The drug-eluting stent delivery system has a balloon disposed about at least a portion of a catheter, the balloon having a first end and a second end and a working length therebetween, the first end and the second end each including a tapered portion, each tapered portion being attached to the catheter, the balloon being inflatable from a collapsed configuration to an inflated configuration. A drug-eluting stent contacts a wall of the blood vessel to maintain the patency of the vessel. The drug-eluting stent has a first end and a second end, the first end and the second end each including a tapered portion, wherein the drug-eluting stent is disposed over the balloon such that at least a portion of the first end and the second end of the balloon are covered by the tapered drug-eluting stent. A method for making the same is also disclosed herein.

6 Claims, 6 Drawing Sheets

(56) References Cited

U.S. PATENT DOCUMENTS

| | | |
|---|---|---|
| 6,179,867 B1 | 1/2001 | Cox |
| 6,251,094 B1 | 6/2001 | Bleam |
| 6,270,521 B1 | 8/2001 | Fischell et al. |
| 6,585,747 B1 | 7/2003 | Limon et al. |
| 6,585,755 B2 | 7/2003 | Jackson et al. |
| 6,770,089 B1 | 8/2004 | Hong et al. |
| 7,105,013 B2 | 9/2006 | Durcan |
| 7,156,869 B1 * | 1/2007 | Pacetti ................ 623/1.11 |

* cited by examiner

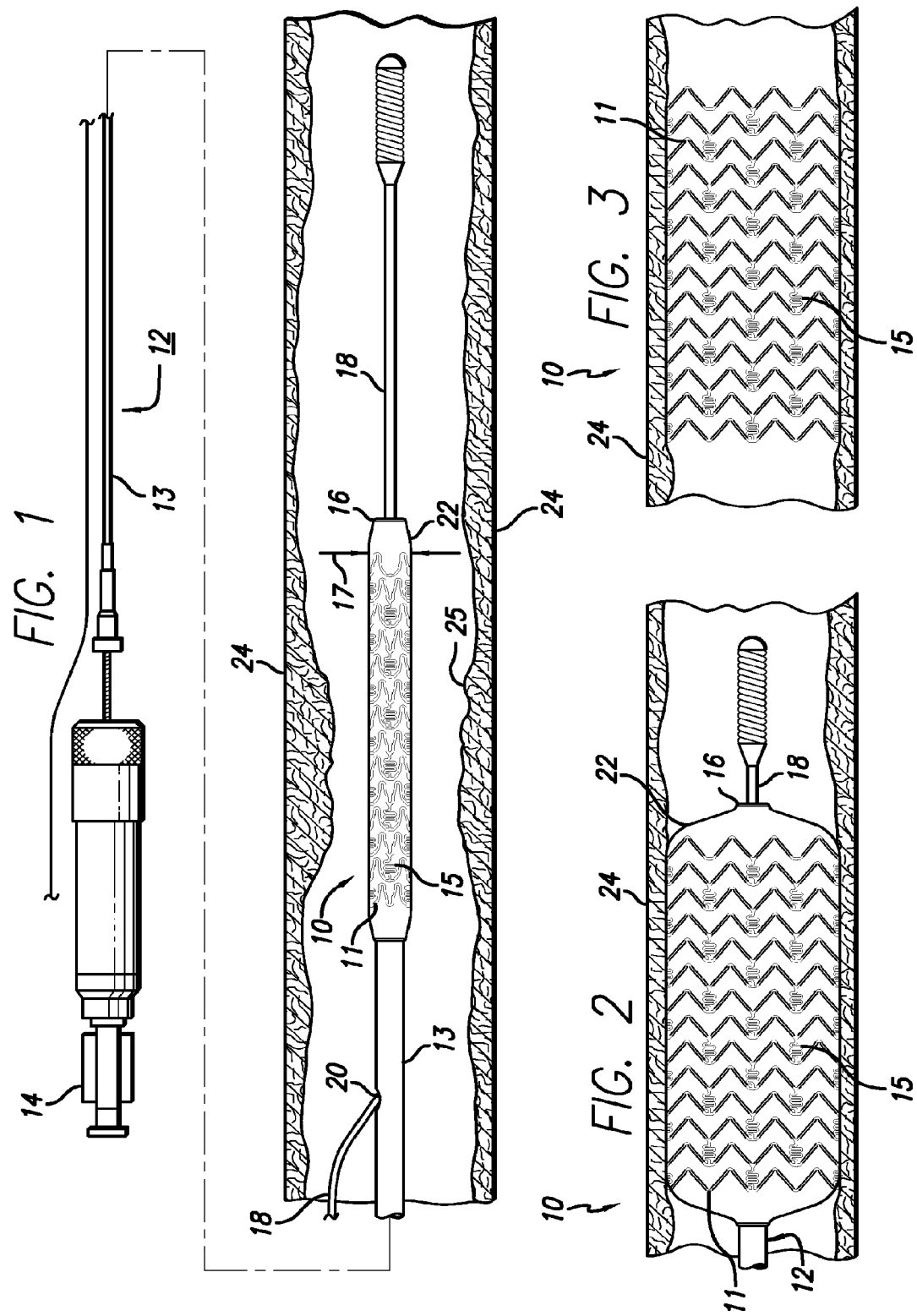

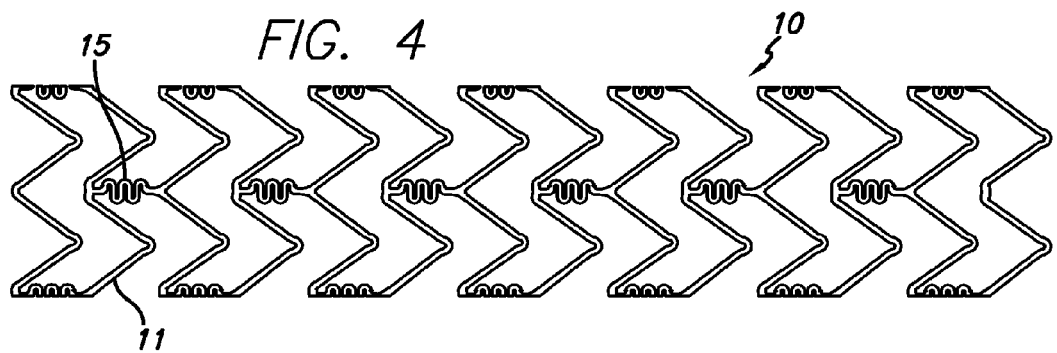
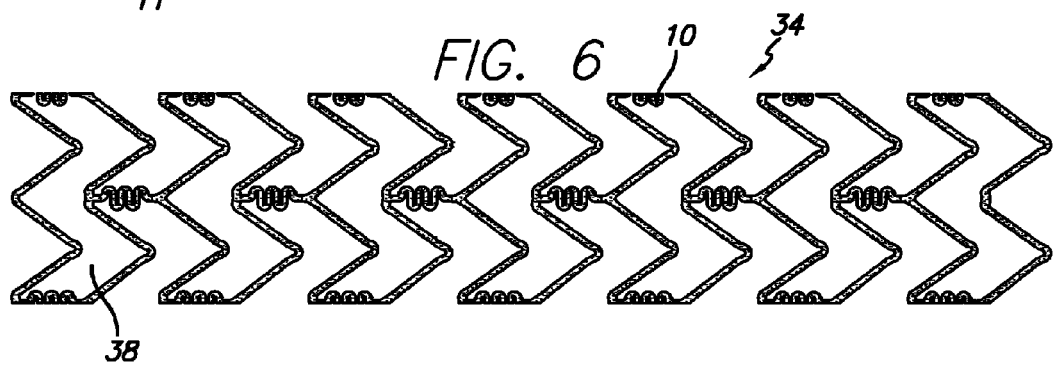
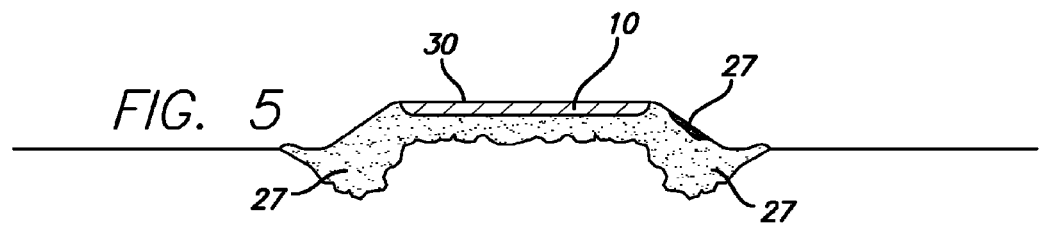
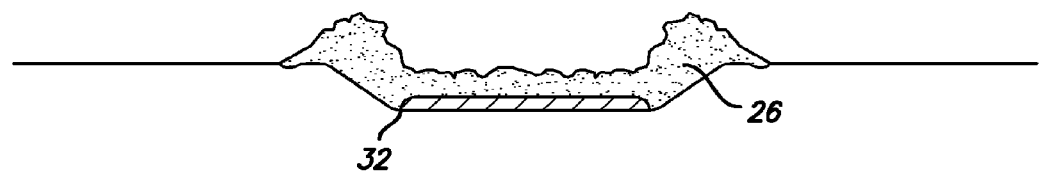
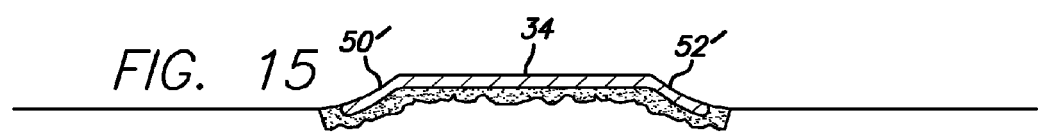
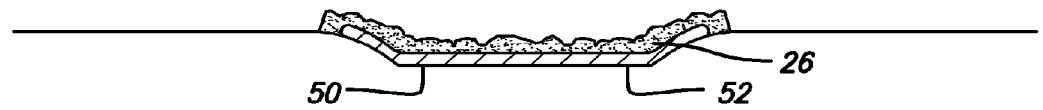

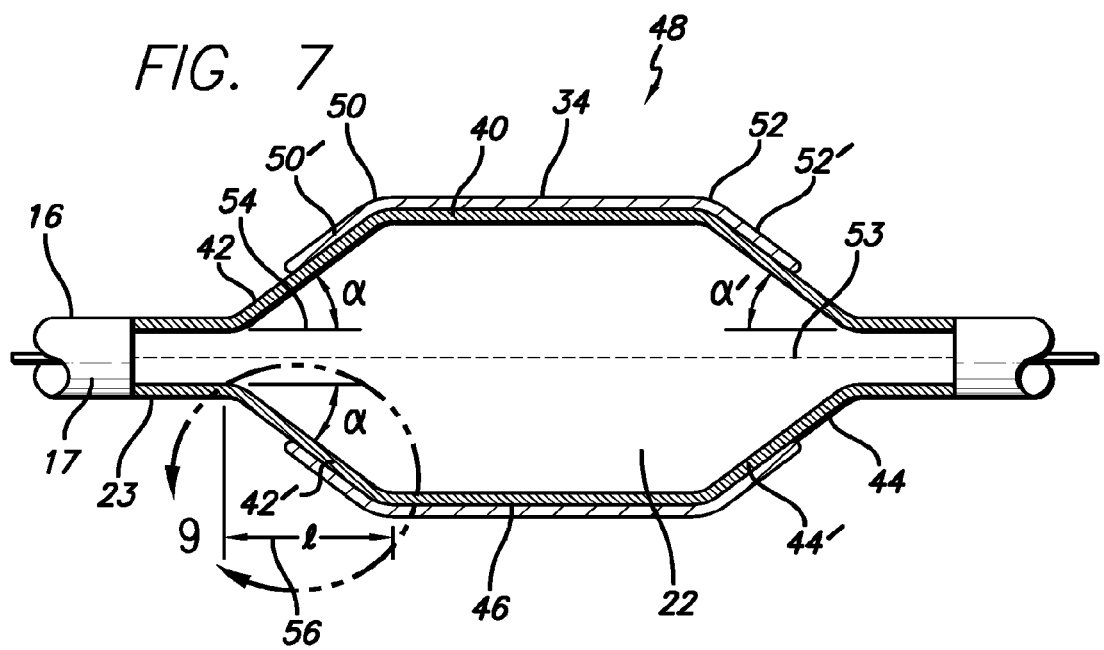
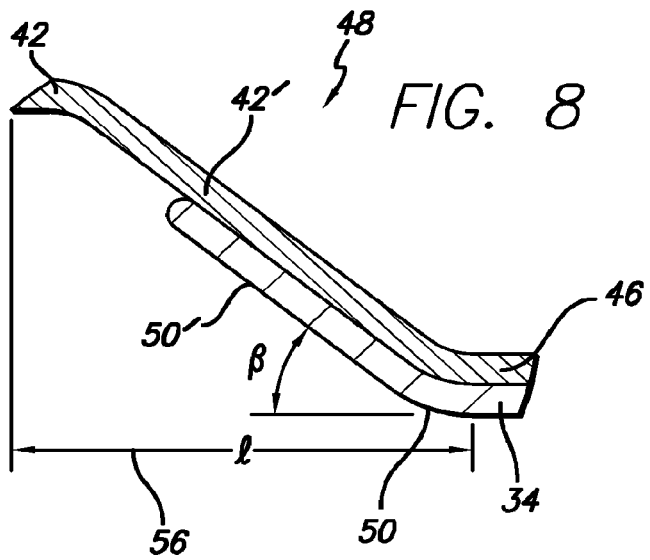

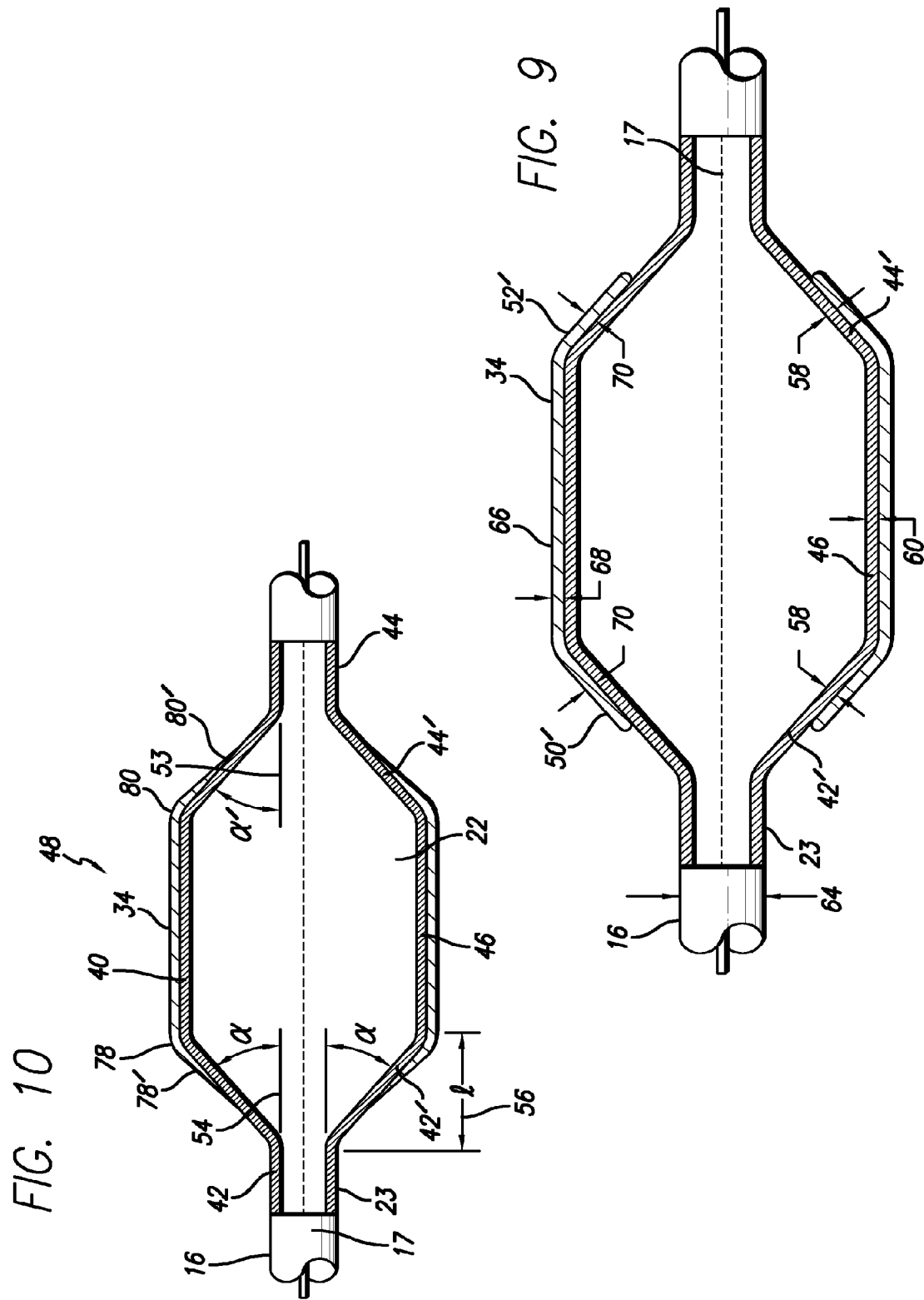

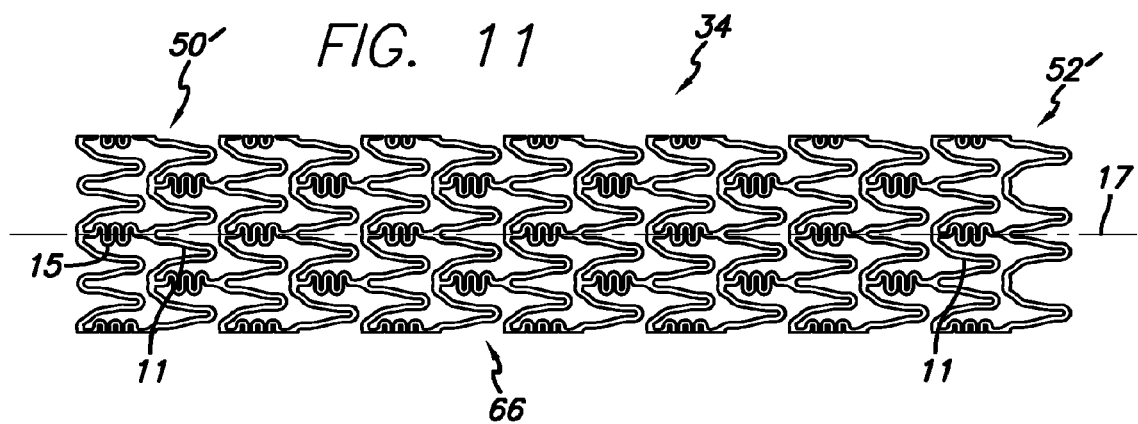
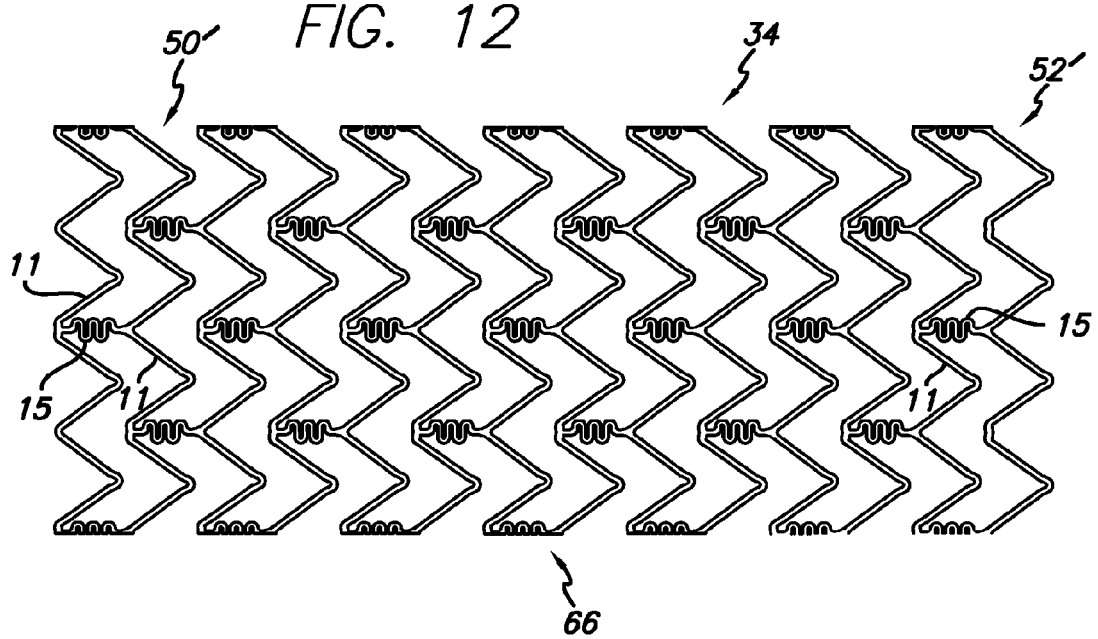

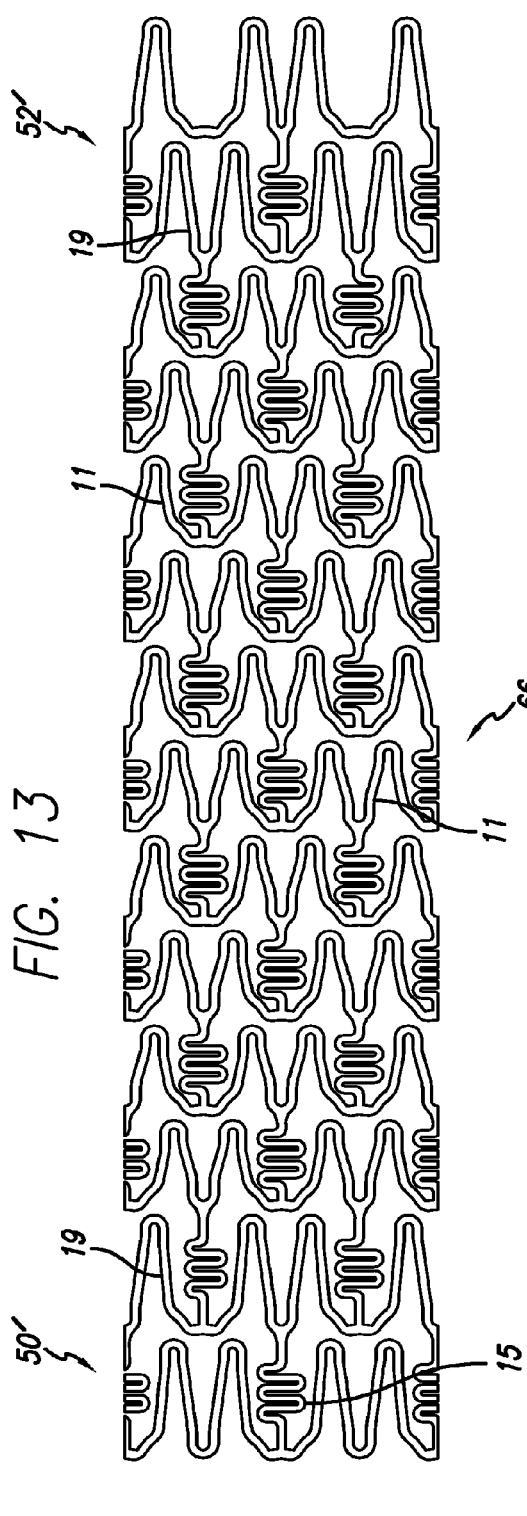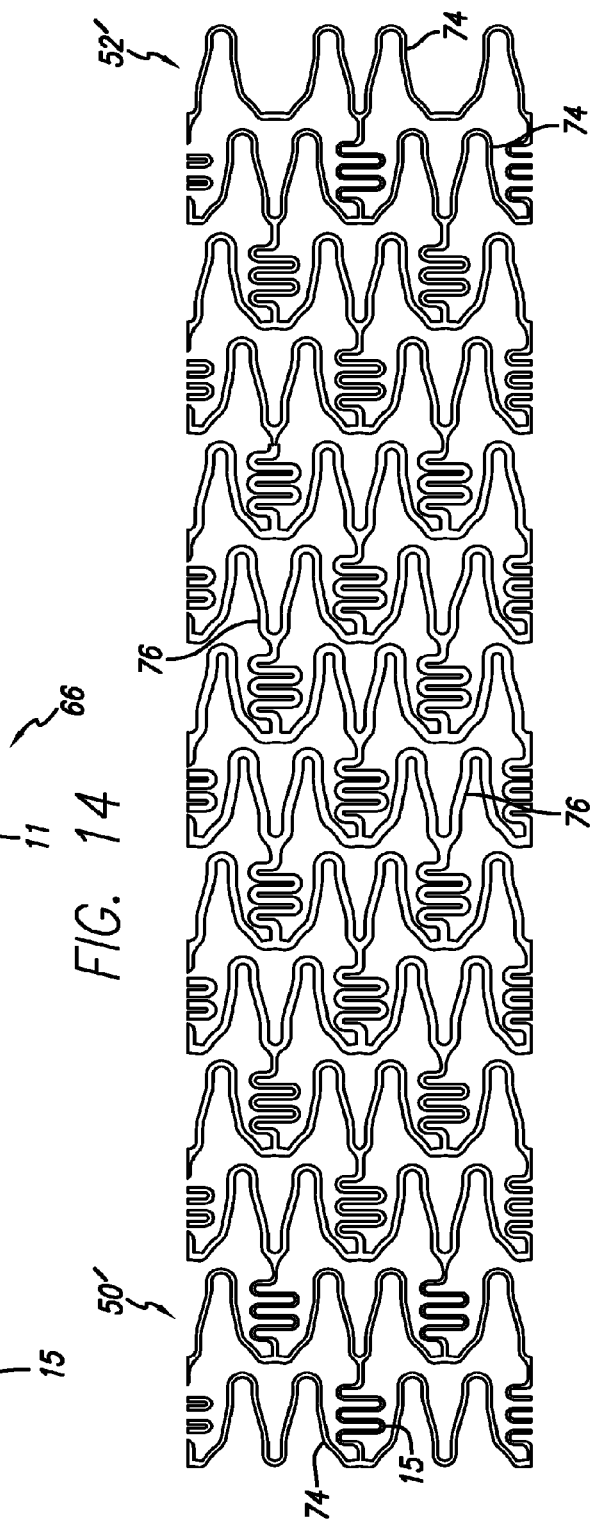

DRUG-ELUTING STENT AND DELIVERY SYSTEM WITH TAPERED STENT IN SHOULDER REGION

CROSS-REFERENCES TO RELATED APPLICATIONS

This application is a division of U.S. Ser. No. 13/727,327 filed Dec. 26, 2012 which is a division of U.S. Ser. No. 13/285,627 filed Oct. 31, 2011, which issued as U.S. Pat. No. 8,343,206 and which is a division of U.S. Ser. No. 11/646,781 filed Dec. 28, 2006, which issued as U.S. Pat. No. 8,057,526 on Nov. 15, 2011 and which is a division of U.S. Ser. No. 10/353,219, filed Jan. 27, 2003, which issued as U.S. Pat. No. 7,156,869 on Jan. 2, 2007, the entire contents of which are hereby incorporated by reference.

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels. More particularly, the invention concerns a tapered drug-eluting stent delivery system consisting of an intravascular device having a local drug-eluting component that is capable of eluting therapeutic drugs with uniform and controlled drug distribution at a treatment site while covering at least a portion of, or all of, a balloon shoulder or taper region such that when deployed the stent extends to the point in the arterial wall where the artery is at reference vessel size.

Intravascular interventional devices such as stents are typically implanted within a vessel in a contracted state, and expanded when in place in the vessel in order to maintain the patency of the vessel to allow fluid flow through the vessel. Stents have a support structure such as a metallic structure to provide the strength required to maintain the patency of the vessel in which it is to be implanted, and are often provided with an exterior surface coating to provide a biocompatible and/or hemocompatible surface. Since it is often useful to provide localized therapeutic pharmacological treatment of a blood vessel at the location being treated with the stent, it is also desirable to provide intravascular interventional devices such as stents with a biocompatible and/or hemocompatible surface coating of a polymeric material with the capability of being loaded with therapeutic agents, to function together with the intravascular devices for placement and release of the therapeutic drugs at a specific intravascular site.

Drug-eluting stent devices have shown great promise in treating coronary artery disease, specifically in terms of reopening and restoring blood flow in arteries stenosed by atherosclerosis. Restenosis rates after using drug-eluting stents during percutaneous intervention are significantly lower compared to bare metal stenting and balloon angioplasty. However, it appears that another phenomena which limits the performance of drug-eluting stent devices has emerged. Recent studies have indicated that the commonly called "candy-wrapper" effect is genuine in drug-eluting stent devices and is a definite limiting factor in their performance. The term "candy-wrapper" effect refers to the occurrence of in-segment or edge restenosis in a vessel treated by intravascular intervention. "Candy-wrapper" ends may result from a non-uniform drug dose at the ends of the stent and/or excessive vessel injury at the stent margins and in the shoulder region. The "candy-wrapper" effect typically starts at the proximal and distal edges of a treatment region and extends outward about 3 mm to 5 mm or more. Several potential reasons for this effect, many of which were first articulated in response to the candy wrapper effects seen with radioactive stents, include the following: (1) balloon injury outside of the stented area; (2) a stimulatory effect on the tissues by the active agent at the lower concentrations outside of the stent; (3) geographic miss during stent placement which implies the stenosis was somewhat there to begin with; and (4) an especially large amount of vessel injury at the stent edge itself as that is a point of maximum wall stress. Of the aforementioned reasons, the first and fourth reasons are the most plausible. Accordingly, if such reasons are true, edge restenosis occurs because the drug tissue concentration falls off rapidly outside of the stent.

What has been needed and heretofore unavailable in the art is a drug-eluting stent delivery system that would be effective in the treatment of edge restenosis within the reference vessel. By minimizing vessel injury outside the stented section of the vessel, the occurrence of edge effects will likely be reduced. Thus, it would be desirable to have a drug-eluting stent that is optimally designed to have tapered end portions so that the region of drug treatment would be extended into the stent shoulder regions of the vessel. The present invention meets these and other needs.

SUMMARY OF THE INVENTION

The present invention is directed to intraluminal devices, and more particularly, to a drug-eluting stent delivery system for the treatment of edge restenosis in the region outside the stented section of a reference vessel. The present invention includes a drug-eluting stent having tapered end portions that extend the region of drug treatment into the stent shoulder regions of the vessel. A method for making such a drug-eluting stent delivery system for implantation within a vessel is also disclosed herein.

The drug-eluting stent embodying features of the invention can be readily delivered to the desired body lumen, such as a coronary or carotid artery (peripheral vessels, bile ducts, etc.), by mounting the drug-eluting stent on an expandable member of a delivery catheter, for example a balloon, and advancing the catheter and drug-eluting stent assembly through the body lumen to the target site. Generally, the drug-eluting stent is compressed or crimped onto the balloon portion of the catheter so that the drug-eluting stent does not move longitudinally relative to the balloon portion of the catheter during delivery through the arteries, and during expansion of the drug-eluting stent at the target site. The drug-eluting stent is relatively flexible along its longitudinal axis to facilitate delivery through tortuous body lumens yet is stiff and stable enough radially in an expanded condition to maintain the patency of a body lumen such as an artery when implanted therein.

The design of the present invention tapered, drug-eluting stent delivery system is not without its challenges. For example, as the stent covers the balloon tapers, during inflation one cannot count on the balloon "dog boning" to maintain the stent on the balloon. In particular, a phenomenon referred to as "watermelon seeding" can occur during stent expansion where the stent "squirts" off to one side. This can be prevented by the dog bone shape of the balloon, which captures the stent. It can be appreciated that processes to improve stent retention are often applied where the balloon outside of the stent is simultaneously heated and pressurized while a physical constraint surrounds the stent to keep the stent from expanding. This process expands the balloon out slightly at just the stent margins to help capture the stent and improve retention. Such processes are not as effective in this case as there are no balloon tapers outside of the stent. One solution to stent retention where the stent covers all, or a portion of, the balloon tapers is to use a process where the entire balloon length is heated and pressurized with a constraint around the system. The stent is imprinted or otherwise partially embedded into the balloon along its entire length so that portions of the balloon extend in between the stent struts, thereby assisting in gripping or holding the stent on the balloon.

In one aspect of the present invention, the drug-eluting stent delivery system of the invention generally provides for a catheter tube. A balloon is disposed about at least a portion of the catheter with the balloon having a first end and a second end and a working length therebetween. Each balloon end includes a tapered portion with each tapered portion being attached to the catheter. The balloon is inflatable from a collapsed configuration, wherein the working length and at least a portion of each tapered portion are substantially flattened to an inflated configuration. The invention further includes a drug-eluting stent that contacts the walls of a lumen to maintain the patency of the vessel with the drug-eluting stent having tapered first and second ends. The drug-eluting stent is disposed over the balloon such that at least a portion of the tapered balloon first and second ends are covered by the drug-eluting stent. A therapeutic drug is loaded into the drug-eluting stent for the eventual release thereof at a treatment site.

As will be appreciated by those having ordinary skill in the art, the drug-eluting stent used in accordance with the present invention can be virtually of any type. Any particular drug-eluting stent described herein is for example purposes and not meant to be limiting of the invention.

The drug-eluting stent further includes a pattern of struts having a plurality of flexible cylindrical rings being expandable in a radial direction with each of the rings having a first delivery diameter and a second implanted diameter while aligned on a common longitudinal axis. At least one link of the drug-eluting stent is attached between adjacent rings to form the drug-eluting stent structure. The pattern of struts can be configured such that the number of cylindrical rings in each tapered portion of the drug-eluting stent first and second ends is less than that in the remainder of the drug-eluting stent. In addition, the number of rings per unit length (i.e., length density) can be less in the tapered regions. The drug-eluting stent includes a central portion that can be expanded to a size greater than that of the reference vessel and the balloon tapered portions.

In one aspect of the present invention, the drug-eluting stent may be formed at least in part of a metallic material. Examples of such metallic materials include stainless steel, platinum, titanium, tantalum, nickel-titanium, cobalt-chromium, and alloys thereof.

The therapeutic drug loaded into the drug-eluting stent of the present invention can include antiplatelets, anticoagulants, antifibrins, antiinflammatories, antithrombins, and antiproliferatives. These foregoing types of therapeutic drugs, used to treat or prevent restenosis, are provided by way of example and are not meant to be limiting, since other types of therapeutic drugs may be developed which are equally applicable for use with the present invention. Furthermore, the calculation of dosages, dosage rates and appropriate duration of treatment are previously known in the art.

In one aspect of the present invention, each tapered portion of the balloon first and second ends has a length in a range of from about 1 mm up to about 10 mm for the taper. A balloon seal (not shown) having a length of from about 0.25 mm up to about 0.5 mm is not included in each balloon tapered portion. The tapered portion of the balloon in the collapsed configuration defines an edge, the edge defining an acute angle measuring between 2 and 30 degrees relative to the longitudinal axis of the catheter. The tapered first and second ends of the balloon are completely covered by the drug-eluting stent. Each tapered portion of the drug-eluting stent first and second ends has a length in a range of from about 1 mm up to about 8 mm, a strut thickness in a range of from about 40 microns up to about 170 microns, and a total outer diameter in a range of from about 0.9 mm up to about 2 mm. The tapered portion of the drug-eluting stent defines an edge, the edge defining an acute angle measuring between 2 and 30 degrees relative to the longitudinal axis of the catheter.

In another aspect, the invention provides a drug-eluting stent delivery system for the treatment of edge restenosis in a blood vessel. The invention includes a tubular catheter. A balloon is disposed about at least a portion of the catheter with the balloon having first and second ends and a working length therebetween. Each balloon end has a tapered portion with each tapered portion being attached to the catheter. The balloon is expandable from a collapsed configuration, wherein the working length and at least a portion of each tapered portion are substantially flattened, to an inflated configuration.

A pattern of struts are interconnected to form a stent structure having a drug-eluting component disposed thereon that contacts the walls of a lumen to maintain the patency of the vessel. In one aspect, at least one of the struts may have a variable thickness. The stent structure and drug-eluting component have first and second ends with each end including a tapered portion. Further, the stent structure and drug-eluting component are disposed over the balloon such that the tapered balloon first and second ends are covered by the stent structure and drug-eluting component. The drug-eluting component can be pre-loaded with a therapeutic drug for the eventual release thereof at a treatment site.

It should be appreciated that the drug-eluting stent delivery system of the present invention may be utilized in any part of the vasculature including neurological, carotid, coronary, renal, aortic, iliac, femoral, or other peripheral vasculature.

An additional aspect of this invention provides a method of making a drug-eluting stent delivery system for the treatment of edge restenosis within a reference vessel. One particular embodiment of making the drug-eluting stent delivery system includes providing a tubular catheter. A balloon is then positioned about at least a portion of the catheter with the balloon having a first end and a second end and a working length therebetween. Each balloon end includes a tapered portion with each tapered portion being attached to the catheter. The balloon is inflatable from a collapsed configuration, wherein the working length and at least a portion of each tapered portion are substantially flattened, to an inflated configuration.

The method of making the drug-eluting stent delivery system of the present invention further includes providing a drug-eluting stent that contacts the walls of a lumen to maintain the patency of the vessel. The drug-eluting stent has a first end and a second end with each end including a tapered portion. The drug-eluting stent is positioned over the balloon such that at least a portion of the tapered balloon first and second ends are covered by the drug-eluting stent. A therapeutic drug can be loaded into the drug-eluting stent for the eventual release thereof at a treatment site.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is an elevational view, partially in section, of a non-tapered stent which is mounted on a delivery catheter and disposed within a damaged artery.

FIG. 2 is an elevational view, partially in section, similar to that shown in FIG. 1 wherein the stent is expanded within a damaged artery.

FIG. 3 is an elevational view, partially in section, depicting the expanded stent within the artery after withdrawal of the delivery catheter.

FIG. 4 is a plan view of a flattened stent of the invention which illustrates the pattern of the stent shown in FIGS. 1-3 in an unexpanded condition.

FIG. 5 is a cross-sectional view of a hypothesized pattern of edge restenosis as a result of injury in the shoulder region of the vessel combined with the absence of drug therapy when a non-tapered stent is used for treatment.

FIG. 6 is a flattened, plan view of a non-tapered stent having a polymer coating disposed thereon.

FIG. 7 is a cross-sectional view of the drug-eluting, tapered stent delivery system in accordance with the present invention;

FIG. 8 is an enlarged, cross-sectional view of the tapered portion of the drug-eluting stent delivery system of FIG. 7;

FIG. 9 is an enlarged, cross-sectional view of the drug-eluting, tapered stent delivery system in accordance with the present invention;

FIG. 10 is a cross-sectional view of an alternative embodiment of the drug-eluting, tapered stent delivery system in accordance with the present invention;

FIG. 11 is a flattened, plan view of a tapered stent with a conformal polymer coating disposed thereon illustrating a reduced number of rings in each shoulder region of the stent;

FIG. 12 is a flattened, plan view of the tapered stent of FIG. 11 in an expanded condition;

FIG. 13 is a flattened, plan view of an alternative embodiment of the drug-eluting tapered stent in accordance with the present invention.

FIG. 14 is a flattened, plan view of the drug-eluting, tapered stent with a variable thickness in accordance with the present invention; and FIG. 15 is a cross-sectional view of a drug-eluting, tapered stent delivery system of the invention with the drug-eluting, tapered stent corresponding to each end of the balloon shoulder region while in the reference vessel.

DETAILED DESCRIPTION OF THE PREFERRED EMBODIMENTS

The present invention is directed to a drug-eluting stent delivery system for the treatment of edge restenosis in a blood vessel. In particular, the present invention includes a drug-eluting stent having tapered end portions that extend the region of drug treatment into the stent shoulder regions of the vessel. Accordingly, as a result of the optimal design of the drug-eluting stent delivery system, balloon injury in the shoulder region is practically non-existent as the tapered drug-eluting stent effectively covers the balloon in this area. A stent that is continuous in the balloon shoulder or taper region, rather than ending abruptly at the start of the shoulder or taper region, along with drug-eluting stent therapy in the shoulder region, can significantly reduce the incidence of edge or in-segment restenosis.

Referring to the drawings, FIG. 1 depicts a metallic (untapered) stent 10 mounted on a catheter assembly 12 which is used to deliver the stent and implant it in a body lumen, such as a coronary artery, carotid artery, peripheral artery, or other vessel or lumen within the body. The stent generally comprises a plurality of radially expandable cylindrical rings 11 disposed generally coaxially and interconnected by undulating links 15 disposed between adjacent cylindrical elements. The catheter assembly includes a catheter shaft 13 which has a proximal end 14 and a distal end 16. The catheter assembly is configured to advance through the patient's vascular system by advancing over a guide wire by any of the well known methods of an over the wire catheter system (not shown) or a rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 of the present invention is used to repair a diseased or damaged arterial wall which may include the plaque 25 as shown in FIG. 1, or a dissection, or a flap which are commonly found in the coronary arteries, carotid arteries, peripheral arteries and other vessels.

In a typical procedure to implant stent 10, the guide wire 18 is advanced through the patient's vascular system by well known methods so that the distal end of the guide wire is advanced past the plaque or diseased area 25. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery 24 after the catheter is withdrawn, as illustrated by FIG. 3. Due to the formation of the stent from an elongated tubular member, the undulating components 15 of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery.

The stent patterns shown in FIGS. 1-3 are for illustration purposes only and can vary in size and shape to accommodate different vessels or body lumens. Further, the metallic stent 10 is of a type that can be used in accordance with the present invention. FIG. 4 is a plan view of a flattened stent which illustrates the pattern of the stent shown in FIGS. 1-3 in an unexpanded condition. The stent can be made to have tapered ends in accordance with the present invention as further disclosed herein. The stent 10 is shown in a flattened condition so that the pattern can be clearly viewed, even though the stent is never in this form. The stent is typically formed from a tubular member, however, it can be formed from a flat sheet such as shown in FIG. 4 and rolled into a cylindrical configuration.

It should be appreciated that the drug-eluting stent delivery system of the present invention is applicable to all vascular stent applications in the body including neurological, carotid, coronary, renal, aortic, iliac, femoral, and other peripheral vasculature.

FIG. 5 illustrates a cross-sectional view of a hypothesized pattern of edge restenosis 26 as a result of injury in the shoulder region of the vessel combined with the absence of drug therapy when a stent 10 (i.e., untapered) is used for treatment. As shown in FIG. 5, the characteristic "candy-wrapper" ends 27 are particularly apparent in the region surrounding the proximal and distal ends of the implanted stent. In addition, the area of the blood vessel where the expanded stent is positioned shows signs of sustained damage 30 from vessel stretch and mechanical damage from the in-stent section itself. Although the stent is not present at the stent shoulder, there is still injury as a result of vessel stretch. Further, there is a significant potential for mechanical injury at the stent edge 32 due to the arterial wall stress accumulation at the stent edge. The tapered, drug-eluting stent delivery system of the present invention resolves the aforementioned issues as a result of the optimal design of the tapered, drug-eluting stent, which is described in further detail herein.

As will be appreciated by those having ordinary skill in the art, the drug-eluting stent 34 used in accordance with the present invention can be virtually of any type. Any particular drug-eluting stent described herein is for example purposes and not meant to be limiting of the invention. FIG. 6 is an example of one such type of drug-eluting stent that may be used in conjunction with the drug-eluting stent delivery system of the invention. In particular, FIG. 6 depicts an elevational view of a stent 10 having a conformal polymer coating 38 disposed thereon. The polymer is adhered to the stent using conventional metal-polymer adhesion techniques, such as by dipping, spraying, wiping, and brushing, which are known in the art. The aforementioned processes may be followed by web clearing operations that can include blowing air or spinning. The conformal polymer coating can have a thickness in the range of about 1 micron to about 10 microns.

In one embodiment, the drug-eluting stent delivery system 48 of the present invention includes a tubular catheter 12 having a longitudinal axis 17, as shown in FIG. 7. A balloon 40 is disposed about at least a portion of the catheter with the balloon having a first end 42 and a second end 44 and a working length 46 therebetween. Each respective first and second end of the balloon has a tapered portion 42ÿ, 44ÿ and a balloon shaft 23 formed integrally with the tubular catheter.

The balloon is inflatable from a collapsed configuration, wherein the working length and at least a portion of each tapered portion are substantially flattened, to an inflated configuration. A drug-eluting stent 34 contacts the walls of a blood vessel to maintain the patency of the vessel. The drug-eluting stent has a first end 50 and a second end 52 with each end including a tapered portion 50ÿ, 52ÿ respectively, of uniform thickness. The drug-eluting stent is disposed over the balloon such that at least a portion of the first and second ends of the balloon tapered portions are covered by the drug-eluting stent. The drug-eluting stent can be pre-loaded with a therapeutic drug, prior to being positioned over the balloon, for the eventual release thereof at a treatment site.

FIG. 8 depicts an enlarged, cross-sectional view of the tapered portion of the drug-eluting stent delivery system 48 of FIG. 7 with the balloon in a collapsed configuration. This collapsed configuration gives the balloon 22 (FIG. 7) of the drug-eluting stent delivery system an optimal profile for insertion into the blood vessel. The collapsed balloon has lateral edges 54 (FIG. 7) which define a taper angle "ÿ" extending from the balloon shaft 23. The edges are defined on the first and second ends of the balloon. In one embodiment, the edges define an angle measuring between 2 and 30 degrees relative to the longitudinal axis 17 of the catheter. The taper angle ÿ has the effect of minimizing friction between the balloon and the blood vessel. The term "collapsed configuration" indicates that the balloon is not completely expanded. In one embodiment, as shown in FIGS. 7 and 8, each respective tapered portion 42ÿ, 44ÿ of the balloon first end 42 and second ends 42, 44 has a length 56. Each of the tapered portions extend a distance, indicated as "l", in a range of from about 1 mm up to about 7 mm. The distance "l" is measured parallel to the catheter longitudinal axis. The respective length for each tapered portion of the balloon first and second ends is the same at each end. The tapered portion 42ÿ, 44ÿ of the balloon is formed integral with the working length 46 and the tubular catheter 12. Accordingly, the taper angle ÿ is formed by the intersection of the balloon tapered portion and the tubular catheter. The angle ÿ is the angle at which the balloon tapered portion meets the working length of the balloon.

With further reference to FIG. 7, each tapered portion 50ÿ, 52ÿ of the drug-eluting stent first and second ends 50, 52, has a length in a range of from about 1 mm up to about 7 mm. The respective length for each tapered portion of the drug-eluting stent first and second ends is the same at each end. The tapered portion of the drug-eluting stent defines an edge 53 which, in turn, defines an acute angle ÿÿ relative to the longitudinal axis of the catheter. In one embodiment, the edge defines an angle measuring between 2 and 30 degrees relative to the longitudinal axis of the catheter. The angle ÿÿ is the angle at which the stent tapered portion extends from the balloon shaft 23. The angle ÿÿ is the angle at which the stent tapered portion meets the working length 46 of the balloon. It can be appreciated that in one embodiment of the invention, the angles ÿ, ÿÿ, ÿ and ÿÿ are equivalent angles and the working length of the balloon is parallel to the tubular catheter.

In accordance with the invention as shown in FIG. 9, the balloon shaft 23, the balloon tapered portions 42ÿ, 44ÿ, and the working length 46 each have respective thicknesses of 58 and 60. The thickness 64 of the tubular catheter distal end 16 is greater than the thickness of the working length. The tapered portion of the balloon tapers from the balloon shaft to the working length. Similarly, a central portion 66 of the drug-eluting stent and the stent tapered portions 50ÿ, 52ÿ each have a respective thickness 68 and 70. The thickness of the tubular catheter distal end 16 is also greater than the thickness of the central portion 66. In one embodiment, each tapered portion of the drug-eluting stent first and second ends 50, 52 may have a strut thickness in a range of from about 25 microns up to about 200 microns.

In an alternative embodiment shown in FIG. 10, the drug-eluting stent 34 tapered portions 78ÿ and 80ÿ of first and second ends 78, 80 can have a decrease in strut thickness with a knife edge. Each tapered portion of the drug-eluting stent may have a strut thickness in a range of from about 25 microns up to about 200 microns.

As illustrated in FIG. 11, the tapered drug-eluting stent 34 further includes a pattern of struts having a plurality of flexible cylindrical rings 11 being expandable in a radial direction, each of the rings having a first delivery diameter and a second implanted diameter and being aligned on a common longitudinal axis 17. At least one link 15 of the tapered drug-eluting stent is attached between adjacent rings to form the drug-eluting stent structure. In order to maintain a consistent metal/artery ratio in the stent first and second end tapers 50ÿ, 52ÿ as in the remainder of the stent, the stent pattern can be changed in the stent first and second end tapers to decrease the amount of metal in such areas, as shown in FIG. 11. The pattern of struts can be configured such that the number of cylindrical rings in each tapered portion of the drug-eluting stent first and second ends is less than that in the remainder of the drug-eluting stent. FIG. 12 is an elevational view of the tapered drug-eluting stent 34 of FIG. 11 in an expanded condition. It should be appreciated that a variety of different configurations are possible to achieve a consistent metal/artery ratio in the taper as in the remainder of the stent, and that the example shown in FIG. 11 is not intended to be limited to such. For example, as shown in FIG. 13, the two outermost end rings at each end can have longer struts 19.

Special consideration may also be given in sizing the tapered drug-eluting stent 34 used in conjunction with the drug-eluting stent delivery system 48 of the present invention. With further reference to FIGS. 11-13, the tapered drug-eluting stent includes the central portion 66 that can be expanded to a size that is greater than that of the reference vessel and the balloon tapered portions 42ÿ, 44ÿ. For example, if the reference vessel size is 3 mm, it may be desirable to have the central portion of the stent expanded to 3.6 mm. However, at the edge of the stent on the balloon taper, it may be desirable to have the stent diameter at 3 mm. Accordingly, the stent in the shoulder regions is intentionally expanded to a different size.

In one embodiment of the invention as shown in FIG. 14, the stent may be formed so that the struts have variable thickness along the stent length. As one example, it is contemplated that struts 74 at the ends of the stent may be narrower than the struts 76 in the center of the stent for purposes of reduced vessel injury at the stent ends. When the balloon first inflates, the balloon ends have a tendency to inflate at a faster rate than the balloon center, however, with narrower struts at the stent ends the balloon, and hence the stent, will expand more uniformly.

FIG. 15 is a cross-sectional view of a drug-eluting, tapered stent corresponding to each end of the balloon shoulder region while positioned within the reference vessel. In one embodiment, the tapered first and second ends of the balloon are partially covered by the drug-eluting stent 34. The degree of coverage is selected so that the stent tapers will completely cover the tapered portion of the vessel wall that is formed when the stent is expanded to a size greater than that of the reference vessel. Therefore, effective drug-eluting stent therapy is provided in the stent shoulder region when the drug-eluting stent is positioned within the vessel.

Examples of various metals or alloys used in forming the stent structure of the present invention drug-eluting stent delivery system include stainless steel, platinum, titanium, tantalum, nickel-titanium, cobalt-chromium, and alloys thereof. Examples of various polymers used in forming the drug-eluting component of the drug-eluting stent delivery system for each of the embodiments include poly(methyl methacrylate) (PMMA), poly(ethylene-co-vinyl alcohol) (EVAL), poly(butyl methacrylate) (PBMA), biodegradable polymers (e.g., polyglycolic acid (PGA) and poly(L-lactic acid) (PLLA)), copolymers and blends thereof. The drug-eluting component may be alternatively fabricated from various metals or alloys, including stainless steel, platinum, titanium, tantalum, nickel-titanium, cobalt-chromium, and alloys thereof.

Examples of therapeutic drugs or pharmacologic compounds that may be loaded into the prefabricated patterned, polymeric sleeve and delivered to the target site in the vasculature include taxol, aspirin, prostaglandins, and the like. Various therapeutic agents such as antithrombogenic or antiproliferative drugs are used to further control local thrombosis. Examples of therapeutic agents or drugs that are suitable for use in accordance with the present invention include sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as CAPTOPRIL® (available from Squibb located in New York, N.Y.), CILAZAPRIL® (available from Hoffman-LaRoche located in Basel, Switzerland), or LISINOPRIL® (available from Merck located in Whitehouse Station, N.J.); calcium channel blockers (such as nifedipine), colchicine, fibroblast growth factor (FGF) antagonists, fish oil (omega 3-fatty acid), histamine antagonists, LOVASTATIN® (an inhibitor of HMG-CoA reductase, a cholesterol lowering drug from Merck), methotrexate, monoclonal antibodies (such as platelet-derived growth factor (PDGF) receptors), nitroprusside, phosphodiesterase inhibitors, prostaglandin inhibitor (available from GlaxoSmithKline located in United Kingdom), seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents are known in the art. The calculation of dosages, dosage rates and appropriate duration of treatment are previously known in the art. Furthermore, the therapeutic drugs or agents are loaded at desired concentration levels per methods well known in the art to render the device ready for implantatation.

In use, the stent is deployed using conventional techniques. Once in position, the therapeutic drug gradually diffuses into adjacent tissue at a rate dictated by the parameters associated with the polymer coat layer. The total dosage that is delivered is of course limited by the total amount of the therapeutic drug that had been loaded within the polymeric conformal coating or other component of the drug-eluting stent. The therapeutic drug is selected to treat the deployment site and/or locations downstream thereof. For example, deployment in the carotid artery will serve to deliver such therapeutic drug to the local arterial tissue, and for very potent drugs, to the brain.

An additional aspect of this invention provides for a method of making a drug-eluting stent delivery system for the treatment of edge restenosis in a blood vessel. In one embodiment, the method includes providing a catheter having a longitudinal axis. A balloon 40 is positioned about at least a portion of the catheter 16, the balloon having first and second ends 42, 44 and a working length 46 therebetween (FIG. 7). Each balloon end includes a tapered portion 44$\ddot{y}$, 44$\ddot{y}$, corresponding to respective first and second ends, with each tapered portion being attached to the catheter. The balloon is inflatable from a collapsed configuration, wherein the working length and at least a portion of each tapered portion are substantially flattened, to an inflated configuration.

The method of making the drug-eluting stent delivery system of the present invention further includes providing a drug-eluting stent 34 (FIGS. 7 and 8) that contacts the walls of a lumen to maintain the patency of the vessel, the drug-eluting stent having first and second ends 50, 52 and each end including a tapered portion 50$\ddot{y}$, 52$\ddot{y}$, respectively. The drug-eluting stent is loaded with a therapeutic drug for the eventual release thereof at a treatment site, such as along the stent shoulder region that corresponds to the balloon tapered portions for the treatment of edge restenosis in the reference vessel. As shown in FIGS. 7 and 8, the means for positioning the drug-eluting stent over the balloon is accomplished in such a manner such that at least a portion of the tapered balloon first and second ends 42$\ddot{y}$, 44$\ddot{y}$ are covered by the drug-eluting stent.

The drug-loaded stent can be processed directly by methods known in the art, such as by spray or dip coating. In this case, for example, the drug/polymer coated stent is first prepared by coating the bare metal stent. Next, the stent is crimped and securely attached to the balloon using current technology to produce the final drug eluting stent delivery system. If a polymeric, drug impregnated, sleeve is used, the sleeve is fabricated separately and then attached to the outer surface of the stent using various metal-polymer and polymer-polymer bonding technologies such as adhesives, solvent welding, or hot melt attachment. This may be done before, or after, the stent is crimped onto the balloon catheter.

The aforedescribed illustrative stent 34, 36 of the present invention and similar stent structures can be made in many ways. One method of making the stent rings 11 is to cut a tubular member, such as stainless steel tubing to remove portions of the tubing in the desired pattern for the stent, leaving relatively untouched the portions of the metallic tubing which are to form the rings. In accordance with the invention, it is preferred to cut the tubing in the desired pattern using a machine-controlled laser process which is well known in the art.

The foregoing laser cutting process to form the cylindrical rings 11 can be used with metals other than stainless steel including cobalt-chromium, titanium, tantalum, platinum, nickel-titanium, and alloys thereof, and other biocompatible metals suitable for use in humans, and typically used for intravascular stents. Further, while the formation of the cylindrical rings is described in detail, other processes of forming the rings are possible and are known in the art, such as by using chemical etching, electronic discharge machining, stamping, and other processes.

While the invention has been illustrated and described, it will be apparent to those skilled in the art that various modifications and improvements can be made without departing from the spirit and scope of the invention. Further, particular sizes and dimensions, materials used, and the like have been described herein and are provided as examples only. Likewise, the invention is not limited to any particular method of forming the underlying medical device structure. Accordingly, it is not intended that the invention be limited, except as by the appended claims.

What is claimed:

1. A stent delivery system, comprising:
   a tubular catheter;
   a balloon about at least a portion of the catheter, the balloon having a first end and a second end and a working length therebetween, the first end and the second end each including a tapered portion, each tapered portion being attached to the catheter, the balloon being inflatable from a collapsed configuration, wherein the working length and at least a portion of each tapered portion are substantially flattened, to an inflated configuration;
   a drug-eluting stent configured to contact a wall of a blood vessel so as to maintain the patency of the vessel, the drug-eluting stent having a first end and a second end, the first end and the second end including a tapered portion;
   the drug-eluting stent having a therapeutic drug coated thereon; and
   the drug-eluting stent being mounted on the balloon such that at least a portion of the first end and the second end of the balloon are covered by the tapered portion of the drug-eluting stent;
   wherein the balloon in a collapsed configuration includes a taper angle of 2° to 30° as measured from lateral edges of the balloon relative to a longitudinal axis of the catheter.

2. The stent delivery system of claim 1, wherein the balloon is formed integrally with the tubular catheter.

3. The stent delivery system of claim 1, wherein the first end and the second end of the stent have a tapered portion having a uniform thickness.

4. The stent delivery system of claim 1, wherein the therapeutic drug is preloaded on an outer surface of the stent prior to mounting the stent on the balloon.

5. The stent delivery system of claim 1, wherein the tapered portion of the first end and the second end of the balloon extends a length in a range from about 1 mm to about 7 mm.

6. The stent delivery system of claim 5, wherein the length of the tapered portions of the first end and the second end of the balloon are substantially equal.

* * * * *

UNITED STATES PATENT AND TRADEMARK OFFICE
CERTIFICATE OF CORRECTION

PATENT NO.        : 8,852,260 B2
APPLICATION NO.   : 14/017548
DATED             : October 7, 2014
INVENTOR(S)       : Stephen Dirk Pacetti It is certified that error appears in the above-identified patent and that said Letters Patent is hereby corrected as shown below:

In the specification:

Column 7, line 66, between "portion" and "and" delete "42ÿ, 44ÿ" and insert instead --42', 44'--.

Column 8, line 7, between "portion" and "respectively" delete "50ÿ, 52ÿ" and insert instead --50', 52'--.
line 20, after "angle" delete "ÿ" and insert instead --"α"--.
line 25, between "angle" and "has" delete "ÿ" and insert instead --α--.
line 29, between "portion" and "of" delete "42ÿ, 44ÿ" and insert instead --42', 44'--.
line 35, before "of the balloon" delete "42ÿ, 44ÿ" and insert instead --42', 44'--.
line 37, between "angle" and "is" delete "ÿ" and insert instead --α--.
line 39, between "angle" and "is" delete "ÿ" and insert instead --β--.
lines 41-42, between "portion" and "of" delete "50ÿ, 52ÿ" and insert instead --50', 52'--.
line 47, between "angle" and "relative" delete "ÿÿ" and insert instead --α'--.
line 50, between "angle" and "is" delete "ÿÿ" and insert instead --α'--.
line 52, between "angle" and "is" delete "ÿÿ" and insert instead --β'--.
lines 54-55, between "angles" and "are" delete "ÿ, ÿÿ, ÿ and ÿÿ" and insert instead --α, α', β and β'--.
line 58, between "portions" and "and" delete "42ÿ, 44ÿ" and insert instead --42', 44'--.
line 67, between "portions" and "each" delete "50ÿ, 52ÿ" and insert instead --50', 52'--.

Column 9, line 5, between "portions" and "of" delete "78ÿ• and 80ÿ" and insert instead --78' and 80'--.
lines 18-19, between "tapers" and "as" delete "50ÿ, 52ÿ" and insert instead --50', 52'--.
line 40, between "portions" and "For" delete ""42ÿ, 44ÿ." and insert instead --42', 44'.--.

Column 11, line 27, between "portion" and "corre-" delete "44ÿ, 44ÿ," and insert instead --42', 44',--.
line 38, between "portion" and "respectively" delete "50ÿ, 52ÿ," and insert instead --50', 52',--.
line 46, between "ends" and "are" delete "42ÿ, 44ÿ," and insert instead --42', 44',--.

Signed and Sealed this
Seventeenth Day of February, 2015

Michelle K. Lee
*Deputy Director of the United States Patent and Trademark Office*